United States Patent [19]

Sölkner

[11] Patent Number: 4,926,043

[45] Date of Patent: May 15, 1990

[54] APPARATUS AND METHOD FOR OPTICAL MEASURING AND IMAGING OF ELECTRICAL POTENTIALS

[75] Inventor: Gerald Sölkner, Ottobrunn, Fed. Rep. of Germany

[73] Assignee: Siemens Aktiengesellschaft, Berlin and Munich, Fed. Rep. of Germany

[21] Appl. No.: 155,103

[22] Filed: Feb. 11, 1988

[30] Foreign Application Priority Data

Mar. 31, 1987 [DE] Fed. Rep. of Germany ....... 3710662

[51] Int. Cl.[5] ............................................. G01R 23/16
[52] U.S. Cl. ............................... 250/231.1; 324/77 K; 350/356
[58] Field of Search ........... 250/231 R; 324/96, 77 K; 350/396

[56] References Cited

U.S. PATENT DOCUMENTS

| | | | |
|---|---|---|---|
| 4,510,441 | 4/1985 | Yasuda et al. | 324/96 |
| 4,595,876 | 6/1986 | Kuhara et al. | 324/96 |
| 4,618,819 | 10/1986 | Mourou et al. | 350/356 |
| 4,631,402 | 12/1986 | Nagatsuma et al. | 324/96 |
| 4,701,697 | 10/1987 | Lübbers et al. | 324/96 |
| 4,786,858 | 11/1988 | Haas et al. | 324/96 |

OTHER PUBLICATIONS

Publication by Valdmanis et al. "Subpicosecond Electrooptic Sampling: Principles and Applications", IEEE Journal of Quantum Electronics, vol. QE-22, No. 1 (Jan. 1986) pp. 69–78.

Publication by Meyer, "Two Dimensional E-Field Mapping with Subpicosecond Resolution", Springer Series in Electro Physics, vol. 21, 1985, pp. 46–49.

Publication by Freeman et al. "Electro-optic Sampling of Planar Digital GaAs Integrated Circuits", Applied Physics Letters, vol. 47, No. 10, Nov. 1985, pp. 1083–1084.

Publication by Weingarten et al. "Direct Electro-Optic Sampling of GaAs Integrated Circuits", Electronics Letters vol. 21, No. 17 Aug. 15, 1985, pp. 765, 766.

*Primary Examiner*—David C. Nelms
*Assistant Examiner*—Stephone B. Allen
*Attorney, Agent, or Firm*—Hill, Van Santen, Steadman & Simpson

[57] ABSTRACT

An apparatus and method include using an electro-optic crystal lying on a component surface, the crystal being coated with a cooperating electrode which is transparent to a sampling laser beam to optically measure and image electrical potentials and voltage levels independently of topographical influences.

17 Claims, 1 Drawing Sheet

APPARATUS AND METHOD FOR OPTICAL MEASURING AND IMAGING OF ELECTRICAL POTENTIALS

BACKGROUND OF THE INVENTION

1 Field of the Invention

The present invention is directed generally to an apparatus and method for optical measurements and/or imaging of electrical potentials using an opto-electric crystal disposed immediately above a specimen.

2 Description of the Related Art

An apparatus for measuring time dependent electrical signals in microelectronic components is known from the publication by K. E. Meyer, "Two-Dimensional E-Field Mapping with Sub Pico Resolution", Springer Series in Electrophysics, volume 21 (1985) pages 46–49. The disclosed apparatus is composed of an electro-optical crystal dielectrically mirrored at one side (see in particular, FIG. 3) that is placed onto a module surface and is scanned point-by-point with a laser beam.

Stroboscopic scanning methods for optical measurements of electrical signals in integrated Ga-As circuits are known from the publication by J. L. Freemen, "Electro-Optic Sampling of Planar Digital Ga-As Integrated Circuits", Appl. Phys. Lett. 47 (10) 1985, pages 1083–1084, and K. J. Weingarten, "Direct ElectroOptic Sampling of Ga-As Integrated Circuits", Electr. Letters, Volume 21, No. 17, pages 765 thru 766.

Further optical measuring methods which exploit the electro-optic effect are described in the publication by J. A. Valdmanis, "Subpicosecond Electro-Optic Sampling: Principles and Applications", *IEEE Journ.* of Quantum Electronics, Volume 22, No. 1 (1986), pages 69 thru 78.

Since only the local electrical micro-fields which are built up in the region of the interconnects in accordance with the interconnect potentials and the topographical conditions are sampled in the known methods and apparatus, it is not possible to derive the potentials or voltages present at various points within the circuit from the acquired measured data without great expense. A precise knowledge of the voltage levels and their fast measurement is a critical prerequisite for checking the operation of microelectronic components.

SUMMARY OF THE INVENTION

An object of the present invention is to provide an apparatus and method in which electrical potentials are optically measured and/or imaged independently of topographical influences. This and other objects are inventively achieved by an apparatus having a first conductive layer arranged immediately above a first electro-optic crystal and by a method characterized by a transparent conductive layer being arranged immediately above the first electro-optic crystal.

An advantage obtained with the invention is that potentials and voltage levels can be identified at arbitrary locations within electronic components independently of the circuit structures present in the environment of the respective measuring points.

Preferred embodiments of the apparatus and advantageous developments of the method include providing a dielectric mirror at a specimen side surface of the first electro-optic crystal, providing a selective reflecting dielectric layer at a specimen-side surface of the electro-optic crystal, or providing an anti-reflection coating at the specimen-side surface of the first electro-optic crystal. A first conductive layer is preferably arranged on a carrier substance. Further improvements include providing a second electro-optic crystal arranged immediately above the first conductive layer, where the second electro-optic crystal has a second conductive layer which is transparent to electro-magnetic radiation and is at a different potential than the first conductive layer. A photo-conductive layer may be applied to the specimen and to the electro-optic crystal. In the method, a preferred embodiment uses different wavelengths for imaging and measuring, and in particular the light used for imaging is acquired from the light used for measuring by frequency doubling.

DESCRIPTION OF THE PREFERRED EMBODIMENTS

Figure 1:
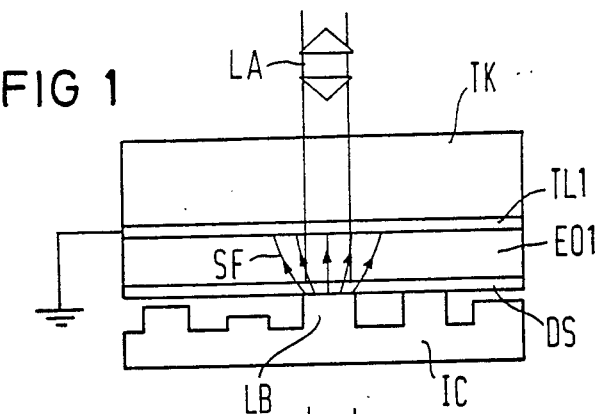
FIG. 1 is a schemmatic illustration of an exemplary embodiment of an inventive apparatus for optical measuring and/or imaging of electrical potentials according to the principles of the present invention.

An apparatus of the present invention is shown schemmatically in FIG. 1 for measuring electrical potentials at arbitrary locations in the interior of a microelectronic component IC. The apparatus is essentially composed of a planeparallel electro-optic crystal EO1, for example of lithium tantalate ($LiTaO_3$) or zinc selenite (ZnSe), resting on a surface of the module or specimen IC, as well as a YAG crystal TK having a specimen side surface coated with a conductive layer TL1, for example of tin oxide. The conductive layer TL1 is transparent for electromagnetic radiation LA, which in particular is a laser emission. Instead of the YAG crystal TK, of course, some other carrier substance, for example, glass, can also be used. Known means are provided for measuring the variations in the reflected electromagnetic radiation LA.

To supress the influences of neighboring interconnects LB interconnects on the micro-fields of the location to be measured, the conductive layer TL1 is brought as close as possible to the specimen or component IC without deteriorating the function thereof due to the high parasitic capacitance, since electrical stray fields SF penetrate the electro-optical crystal EO1 nearly perpendicularly at least above a current carrying interconnect LB. The conductive layer TL1 is also referred to as the cooperating electrode and generally lies at ground potential. The electro-optical effect, or Pockels effect, in the apparatus of the invention is dependent only on the interconnect potential or on the difference in the potential present between the interconnect LB and the cooperating electrode TL1. The electro-optical effect does not depend on the penetration depth of the electrical stray fields SF (voltage contrast). It is thereby possible to optically identify potentials and voltage levels independently of topographical influences. Such identification takes place with the assistance of the laser beam LA which is positioned to impinge the appertaining interconnect LB and which is preferably polarized (see, for example, the publications cited herein above).

The surface of the electro-optic crystal EO1 on the specimen side is dielectrically mirrored at DS to reflect the polarized laser beam LA and thus vary the polarization of the reflected beam LA for detecting the electrical stray fields SF. Since this mirror coating DS makes positioning of the laser probe LA to the measuring location more difficult (due to reduced contrast), a selectively reflecting single layer or multi-layer mirroring DS is advantageous. This layer DS completely reflects the radiation wavelength used for making the potential measurement but only partially reflects the radiation wavelength used for seeking the measured location or used for large-area imaging of the component surface. The radiation used for imaging the component surface, for example, can be acquired from the radiation used for measurement by frequency doubling in a non-linear medium before the beam LA reaches the specimen IC so that only a single radiation source is required.

To reduce the interference effects which deteriorate the image quality at the boundary surfaces between the dielectric mirror and air, or between air and the component, it is advantageous to replace the dielectric mirror DS with an anti-reflection coating.

As shown in FIG. 1, different ones of the interconnects LB may be arranged at different levels. This may be, for example, for reasons of production engineering. One will therefore generally not succeed in bringing all interesting measuring points into contact with the electro-optic crystal EO1 simultaneously. To compensate for such height differences, a photo-conductive layer PL shown in FIG. 2 is applied between the component surface IC and the partially reflecting dielectric mirrored electro-optic crystal EO1, or, respectively the electro-optic crystal EO1 provided with an anti-reflection coating.

Figure 2:
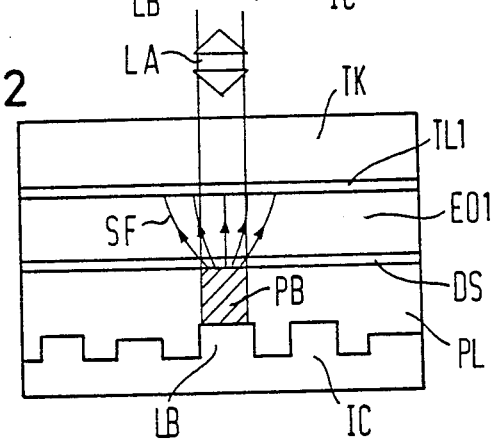
FIG. 2 is a schemmatic representation of a second embodiment of the present invention.

In the apparatus shown in FIG. 2, with the electro-optic effect also is dependent only on the interconnect potential to be measured, since a photo-conductive region PB which is generated in the photo-conductive layer PL by the non-reflected radiant intensity is effective to short the non-reflective or partially reflecting layer DS to the respective interconnect LB.

To further reduce geometry dependent effects and influences of neighboring interconnects on the micro-fields in the voltage measurement, it is advantageous to place the transparent cooperating electrode TL1 at a negative potential for positive interconnect potentials, or positive potential for negative interconnect potentials. For example, the voltage applied to the electrode TL1 is $V_O = \pm 100$ volts.

Figure 3:
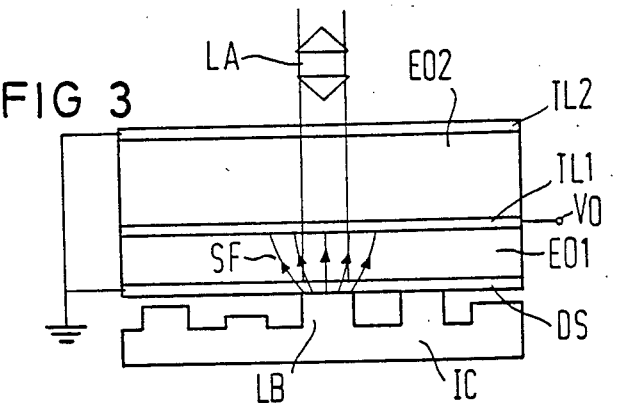
FIG. 3 is a schemmatic representation of a further embodiment of the present invention.

For compensating the birefringence induced in the electro-optic crystal EO1 by the charged cooperating electrode, it is inventively proposed to arrange a second electro-optic crystal EO2 immediately above the cooperating electrode TL1 as shown in FIG. 3. This second electro-optic crystal EO2 includes a conductive layer TL2 which is transparent to the sampling laser beam LA. The layer TL2 advantageously lies at the same potential as the dielectric mirror DS, which usually lies at ground potential. The same voltage drop, thus, appears across the electro-optic crystal EO1 as across the electro-optic crystal EO2.

Since the phase difference $\Delta\phi$ between an ordinary ray and an extraordinary ray in Pockel's crystal is proportional to a product E·d (where E and d refer to the electrical field strength in the crystal and the path traversed by the laser beam in the electrical field, respectively) is proportional to the voltage difference $V_O$ in the present case, the equation $$\Delta\phi_1 = -\Delta\phi_2$$

refers to the inventive apparatus of FIG. 3. Thus, only the electrical interconnect fields vary the polarization condition of the laser beam LA. $\Delta\phi_1$ and $\Delta\phi_2$ refer to the phase shifts produced in the electrode-optic crystals EO1 and EO2 by the charged cooperating electrode TL1.

In the apparatus of FIG. 3, a photo-conductor may also be applied between the component surface and the partially reflecting dielectrically mirrored electro-optic crystal EO1, or in an alternate embodiment the electro-optic crystal EL1 provided with an anti-reflection coating.

An exemplary apparatus of the invention having the following layer thicknesses d is used for investigating an electronic component having an active surface of about $1 \times 1$ cm$^2$:

| | | |
|---|---|---|
| electro-optic crystal | EO1 | $d_{EO1} \gtrsim 50$ μm |
| dielectric mirror | DS | $d_{DS} \simeq 100$ nm |
| transparent cooperating electrode | TL1 | $d_{TL1} \simeq 100$ nm |
| carrier crystal | TK | $d_{TK} \simeq 0.5$ mm |
| electro-optic crystal | EO2 | $d_{EO2} \simeq 0.5$ mm |
| transparent conductive layer | TL2 | $d_{TL2} \simeq 100$ nm. |

The layer thickness to be respectively selected in each instance is to be matched to the experimental conditions.

Although other modifications and changes may be suggested by those skilled in the art, it is the intention of the inventor to embody within the patent warranted hereon all changes and modifications as reasonably and properly come within the scope of his contribution to the art.

I claim:

1. An apparatus for optical measuring and imaging of electrical potentials, comprising:
   a first electro-optic crystal disposed above a specimen;
   a first conductive layer disposed immediately above said first electro-optic crystal, said first conductive layer being transparent at least to electromagnetic radiation used for measurement; and
   a dielectric mirror at a specimen side surface of said first electro-optic crystal.

2. An apparatus as claimed in claim 1, wherein said dielectric mirror is a selectively reflecting dielectric layer at a specimen side surface of said first electro-optic crystal for reflecting selected wavelengths.

3. An apparatus as claimed in claim 1, further comprising:
   a carrier substance on which said first conductive layer is arranged.

4. An apparatus as claimed in claim 1, further comprising:
   a second electro-optic crystal disposed immediately above said first conductive layer, said second electro-optic crystal having a second conductive layer that is transparent to at least electromagnetic radiation used for measurement; and
   means for establishing different potentials at said first and second conductive layers.

5. An apparatus as claimed in claim 1, further comprising:

a photo-conductive layer between the specimen and said first electro-optic crystal.

6. An apparatus for optical measuring and imaging of electrical potentials, comprising:
   a first electro-optic crystal disposed above a specimen;
   a first conductive layer disposed immediately above said first electro-optic crystal, said first conductive layer being transparent at least to electromagnetic radiation used for measurement; and
   an anti-reflection coating at a specimen side surface of said first electro-optic crystal so that radiation used for measurement is reflected from a surface of the specimen.

7. An apparatus as claimed in claim 6, further comprising:
   a second electro-optic crystal disposed immediately above said first conductive layer, said second electro-optic crystal having a second conductive layer that is transparent to at least electromagnetic radiation used for measurement; and
   means for establishing different potentials at said first and second conductive layers.

8. An apparatus as claimed in claim 6, further comprising:
   a photo-conductive layer between the specimen and said first electro-optic crystal.

9. A method of optical measuring and imaging of electrical potentials, comprising the steps of:
   arranging a first electro-optic crystal immediately above a specimen;
   arranging a transparent conductive layer immediately above said first electro-optic crystal;
   directing a polarized light ray through said first electro-optic crystal and said transparent conductive layer to at least one point on a surface of the specimen;
   detecting modification of a polarization condition of said light ray reflected from a reflecting surface, said reflecting surface being one of a surface of the specimen and a surface of a dielectric mirror.

10. A method as claimed in claim 9, further comprising:
    providing a dielectric mirror at a specimen side surface of said first electro-optic crystal.

11. A method as claimed in claim 9, further comprising:
    coating a specimen side surface of said first electro-optic crystal with a selectively reflecting layer.

12. A method as claimed in claim 9, further comprising:
    applying a first conductive layer to a carrier substrate.

13. A method as claimed in claim 9, further comprising:
    arranging a second electro-optic crystal having a second conductive layer transparent to said light ray immediately above said first conductive layer; and
    applying different potentials to said first and second conductive layers.

14. A method as claimed in claim 9, further comprising:
    covering a surface of said specimen with a photo-conductive layer.

15. A method as claimed in claim 9, further comprising:
    coating a specimen side surface of said first electro-optic crystal with an anti-reflection coating.

16. A method as claimed in claim 15, further comprising:
    using light of different wavelengths for imaging and measuring.

17. A method as claimed in claim 16, further comprising:
    acquiring light used for imaging from light used for measuring by frequency doubling.

* * * * *